(12) United States Patent
Eger

(10) Patent No.: US 6,293,675 B1
(45) Date of Patent: Sep. 25, 2001

(54) MACULAR STRESSMETER

(75) Inventor: Elmer H. Eger, 408 E. Seneca St., Ithaca, NY (US) 14850

(73) Assignee: Elmer H. Eger, Ithaca, NY (US)

( * ) Notice: Subject to any disclaimer, the term of this patent is extended or adjusted under 35 U.S.C. 154(b) by 0 days.

(21) Appl. No.: 09/560,497

(22) Filed: Apr. 27, 2000

Related U.S. Application Data
(60) Provisional application No. 60/142,965, filed on Jul. 12, 1999.

(51) Int. Cl.$^7$ .................................................. A61B 3/02
(52) U.S. Cl. .............................................................. 351/224
(58) Field of Search .................................. 351/200, 201, 351/202, 203, 211, 221, 237, 224, 246, 208; 600/558

(56) References Cited

U.S. PATENT DOCUMENTS

| | | | |
|---|---|---|---|
| 3,245,315 | 4/1966 | Marks et al. | 88/61 |
| 4,541,697 | 9/1985 | Remijan | 351/211 |
| 4,545,658 | 10/1985 | Weiss | 351/222 |
| 4,822,162 | 4/1989 | Richardson et al. | 351/243 |
| 5,080,478 | * 1/1992 | O'Brien et al. | 351/224 |
| 5,099,858 | 3/1992 | Hofeldt | 128/745 |
| 5,139,030 | 8/1992 | Seay, Jr. | 128/745 |
| 5,646,710 | 7/1997 | Caskey | 351/223 |
| 5,838,422 | 11/1998 | Caskey | 351/223 |
| 5,873,831 | 2/1999 | Bernstein et al. | 600/473 |
| 5,919,132 | 7/1999 | Faubert et al. | 600/318 |
| 6,176,581 | * 1/2001 | Newsome | 351/224 |

OTHER PUBLICATIONS

Severin, Capt Sanford L. et al., "Photostress Test for the Evaluation of Macular Function," Arch of Ophthalmology, Nov. 1963 70 (5), pp. 593–597.

Severin, Sanford L., M.D., "Macular Function and the Photostress Test 1," Arch Ophthal, vol. 77, Jan. 1967, pp. 2–7.

Severin, Sanford L., M.D., "Macular Function and the Photostress Test 2," Arch Ophthal, vol. 77, Feb. 1967, pp. 163–167.

Glaser, Joel S., M.D., "The Photostress Recovery Test in the Clinical Assessment of Visual Function," Am J of Ophthalmology, Feb. 1977, 83 (2), pp. 255–260.

Gomez–Ulla, F. et al., "Macular dazzling test on normal subjects," British Journal of Ophthalmology, Mar. 1986, 70(3)., pp. 209–213.

Zabriskie, Norman A., M.D., "The Pupil Photostress Test," Ophthalmology, Jun. 1994; 101 (6), pp. 1122–1130.

* cited by examiner

Primary Examiner—George Manuel
(74) Attorney, Agent, or Firm—Webb Ziesenheim Logsdon Orkin & Hanson, P.C.

(57) ABSTRACT

A portable, integrated, hand-held visual examination apparatus for conducting a photostress test on the retina of the human eye. The apparatus includes, within the housing, a timing mechanism, a flash mechanism and an input device, for activating these mechanisms.

20 Claims, 2 Drawing Sheets

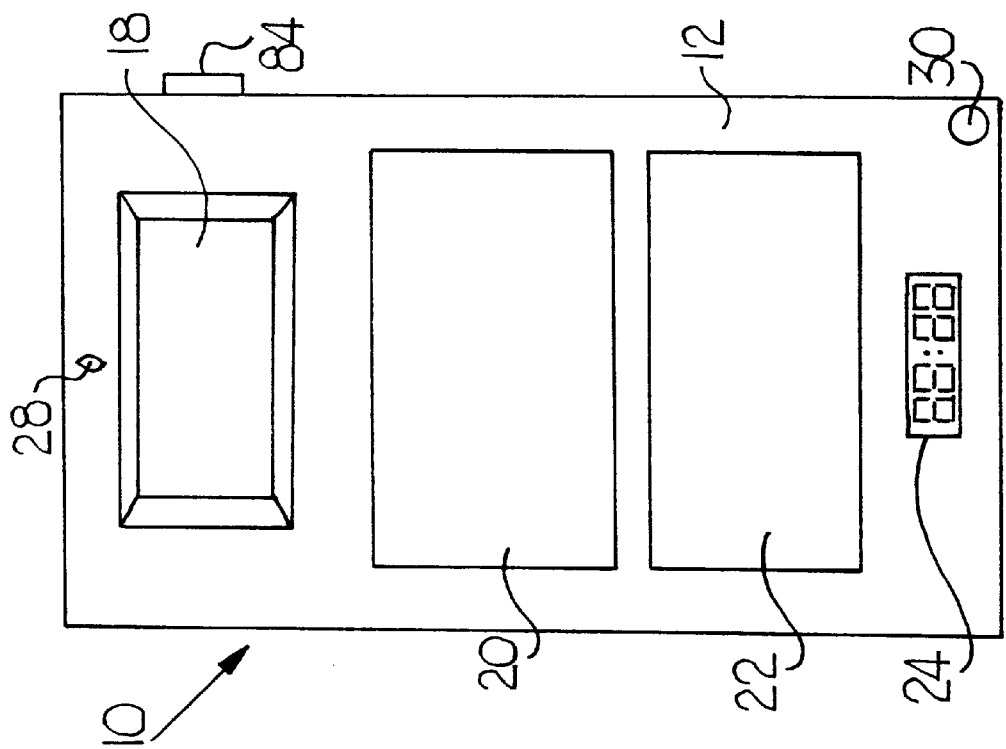
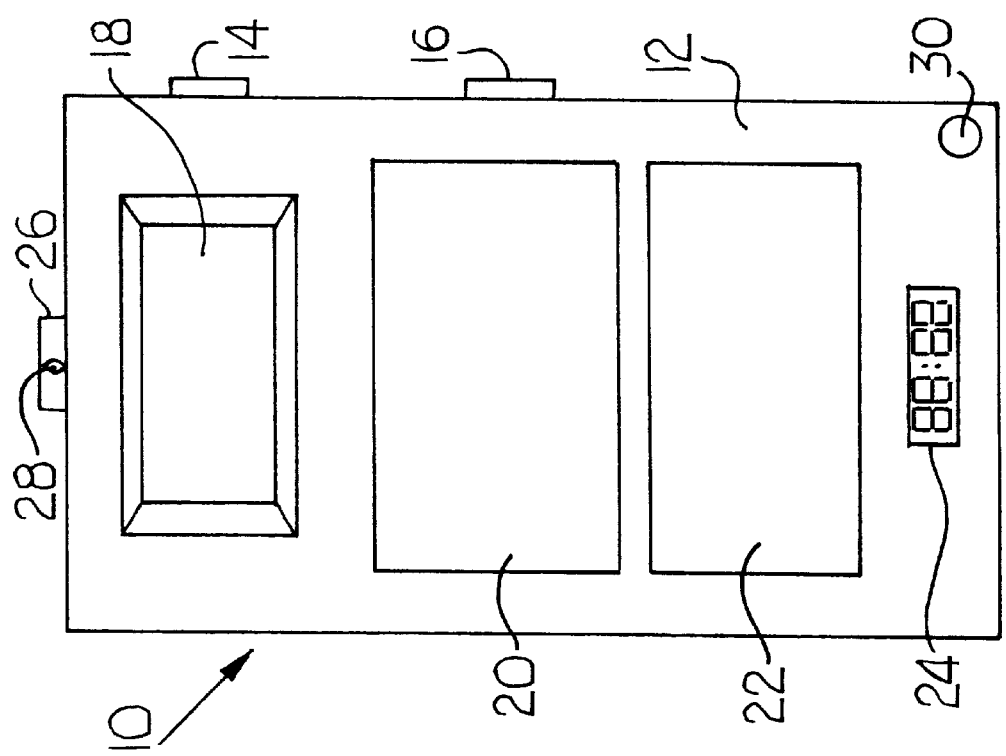

MACULAR STRESSMETER

CROSS-REFERENCE TO RELATED APPLICATIONS

This application claims the benefit of U.S. Provisional Application No. 60/142,965 filed Jul. 12, 1999.

BACKGROUND OF THE INVENTION

1. Field of the Invention

The present invention relates generally to portable visual examination apparatus and, in particular, to a hand-held instrument for bleaching the macula of the human retina and measuring its recovery time.

2. Description of the Prior Art

The retina of the human eye consists of several layers, including a layer of nerve cells and fibers and a deeper layer of rods and cones. Cones differ from rods in that the cones provide a human with color and detailed vision, whereas rods differentiate black/white and motion. This layer of rods and cones is the light-sensitive layer. Located in a small central area of the retina is the macula, which houses the higher concentration of cones. Further, within the macula, the highest concentration of cones resides in the fovea.

Macular photostress testing is a sensitive method for detecting patients with macular disturbances, such as cystoid macula edema, central serous choroidopathy and senile macular degeneration. These disturbances have been shown to cause a significantly prolonged recovery from photostress.

It is well known in the art that exposing the macula of the human retina during an ophthalmoscopic examination to a bright light requires a certain amount of time for the human eye to recover useable visual acuity. This return time is commonly referred to as "recovery" time and varies from individual to individual. In many individuals, an unusually long recovery time is encountered after this photostressing or bleaching. This lengthened recovery time may be an indication of subliminal or developing maculopathy or other retinal disease. A recovery rate longer than normal helps the doctor identify persons at risk for developing macular degeneration or other retinal disease. In addition, a photostress test is particularly helpful in following intra-ocular surgery when cystoid macular edema is suspected. An increase in or lengthy recovery time indicates a maculopathy and helps to rule out other complicating factors, such as irregular astigmatism, early capsular opacification or optic nerve disease.

In assessing recovery time, there are various methods for definitively marking the point of re-focus (or recovery). A Snellen Eye Chart or an Amsler grid are two examples of tools used in marking the point of re-focus. A Snellen Eye Chart is a well-known chart consisting of lines of gradually reduced-sized letters. Typical Amsler grids, with focusing improvements, are disclosed in U.S. Pat. No. 5,646,710 to Caskey and U.S. Pat. No. 5,838,422 to Caskey. Further, U.S. Pat. No. 5,139,030 to Seay, Jr. discloses an Amsler grid with an illuminated center to assist the patient in focusing on the center of the grid. A Snellen Eye Chart may be utilized in determining the recovery time between bleaching of the retina to the return of visual acuity. While the Amsler grid may be used to assess recovery time, it is typically used as a screening device to ascertain loss or distortion of central or macular vision.

A flash unit, a timer and a focusing device have been previously combined together to create a visual examination apparatus for testing for macular degeneration. For example, U.S. Pat. No. 4,545,658 to Weiss discloses the use of such a combination for administering the photostress recovery test. However, the disadvantage of the Weiss apparatus is its requirement to be housed in a large, non-portable cabinet. While this cabinet-enclosed photostress instrument assists in normalizing the photostress procedure and simplifying the focusing process, the overall unit is large, cumbersome and is burdened with a split imaging mirror. In addition, such an instrument requires standalone optotype slides and continual administrative interaction.

SUMMARY OF THE INVENTION

It is therefore an object of the present invention to provide a portable, hand-held combined photostress testing apparatus that is easy and inexpensive in its manufacture. It is another object of the present invention to provide an apparatus that can be mass-distributed for use in both clinical and research situations. It is a further object of the present invention to provide an apparatus that is standardized to assist in advancing the art and determining retinal diseases.

The present invention is a hand-held, portable photostress visual examination device including a housing or body, which contains a controllable flash unit, a controllable timing unit, an optional back-lighting unit for an optotype chart, a controllable power source and electronic circuitry associated with these units. Connected to the housing may be an on/off switch, simultaneous flash and timer switch, a timer stop switch, a visual timing display for the timing unit and the recovery chart. Further, an Amsler or other grid may be provided on the body as an auxiliary tool. The recovery chart can be a Snellen Eye Chart or any suitable optotype chart for assessing an eye's return to a state of visual acuity. In addition, a color discrimination or contrast sensitivity test can be used. A measuring unit, such as retractable tape or string, may be attached to the top of the housing, allowing the examiner to quickly and accurately measure the appropriate distance between the device and the eye.

To use the invention, one of the patient's eyes is occluded and the patient reads, at a standard reading distance of 13–16 inches, the smallest definable line on the optotype chart on the face of the housing, using the patient's best optical reading correction. The measurement is recorded in near point Snellen or other standard ophthalmic terms. The patient's optical reading correction is removed, if such correction was required. The invention is moved to a closer, standardized distance from the non-occluded eye, using the measuring device, e.g., the retractable tape or string. The patient then gazes at the center of the flash unit, as viewed from the front side of the device. Next, the simultaneous flash and timer button is actuated, flashing the flash unit and starting the timing unit. Once "flashed", the patient replaces any spectacle correction and attempts to read the line of optotypes immediately above the initially read line at the original reading distance. When the line of optotypes immediately above the initially read line is readable, the timer stop button is actuated, the timing unit ceases and the examiner reads the time from the visual timing display.

These and other advantages of the present invention will be clarified in the brief description of the preferred embodiments taken together with the attached figures wherein like reference numerals represent like elements throughout.

BRIEF DESCRIPTION OF THE DRAWINGS

FIG. 1 shows a front view of a hand-held visual examination device according to the present invention;

FIG. 3 shows a front view of a second embodiment of a hand-held visual examination device according to the present invention.

DETAILED DESCRIPTION OF THE PREFERRED EMBODIMENTS

Figure 2:
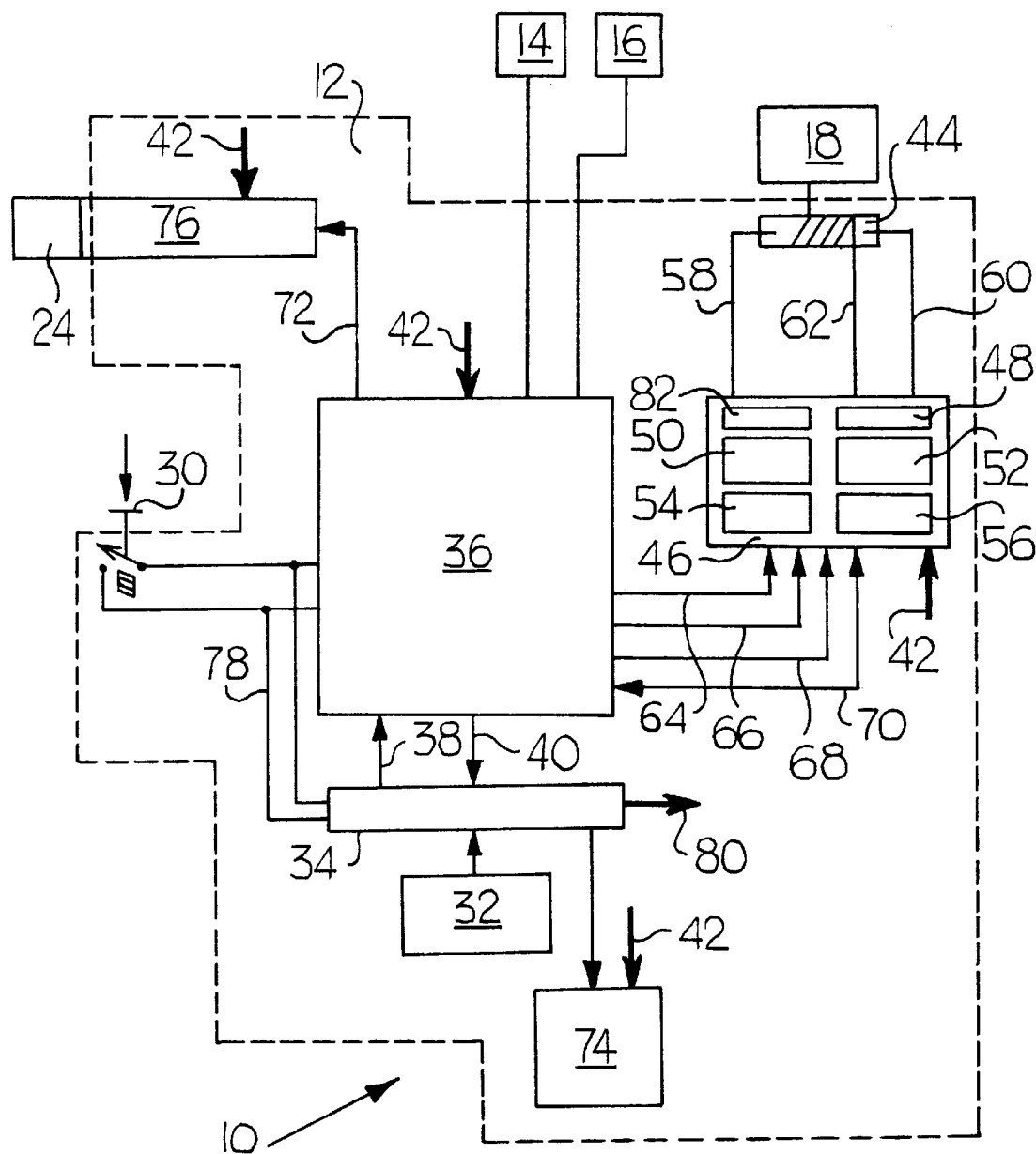
FIG. 2 shows a block diagram of the device shown in FIG. 1 illustrating the internal components and flow of the internal components of the device.

The present invention is a portable, integrated, hand-held visual examination device 10 and method of using the apparatus for detecting macular degeneration and other retinal diseases. As seen in FIG. 1, the device 10 of the present invention includes a housing 12 or body, which houses the internal components of the device 10. Attached to the housing 12 is a simultaneous flash and timer switch 14. Also attached to the housing 12 is a timer stop switch 16. On the face of the device 10 is a flash unit screen 18, an Amsler or other grid 20, an optotype chart 22 (such as a Snellen Eye Chart) and a timer visual display 24. Further, a measurement unit in the form of a retractable tape or string mechanism 26 can be mounted on or within the housing 12, with a tape or string outlet 28 allowing a certain length of tape or string to be pulled from the outlet 28 and retracted back into the retractable tape or string mechanism 26. This retractable tape or string mechanism 26, is integral with (either attached to or within) the housing 12, as shown in FIGS. 1 and 3. In addition, an on/off switch 30 is located on the housing 12. While FIG. 1 shows one typical arrangement of the parts as attached to the housing 12, it should be appreciated by one skilled in the art that various arrangements of the components are equally functional.

Turning to the internal components of the device 10, FIG. 2 schematically illustrates the connection, flow and operation of the various components. The device 10 is powered by power source 32, which communicates through a power controller 34, producing a power output 80. The power controller 34 communicates with the central logic controller 36. This logic controller 36 controls the electronic and internal aspects of the device 10 and may be discrete logic devices or a ROM-based microcontroller. The logic controller 36 receives the power source status 38 from the power controller 34 and returns a "turn off" signal 40, if required. The power output 80 is delivered to the various components that require power via a power input 42. When the operator activates the on/off switch 30, a "turn on" signal 78 is sent to the power controller 34. It is also envisioned that different power controllers 34, such as logic-controlled voltage regulators, may be used. While the logic controller 36 may always be on, as when not being used, the logic controller 36 enters a "sleep mode", using a very low current.

A flash lamp 44 is connected with and in communication with a flash controller unit 46, which includes a current converter 48, a charge switch 50, a trigger switch 52, a trigger transformer 54, a discharge switch 56, and a storage capacitor 82. Overall, the flash controller unit 46 communicates with the flash lamp 44 via an anode 58, a cathode 60 and a flash trigger 62. The logic controller 36 interfaces with the flash controller 46 (and its various components), transmitting and receiving a charge signal 64, a trigger signal 66, a discharge signal 68 and a trigger ready signal 70. Also communicating with the logic controller 36 is the timer visual display 24, which may be static or dynamic. The logic controller 36, which interfaces with, or is integral with, a timing mechanism 76, transmits a status/time data signal 72 to the timer visual display 24. Finally, the logic controller 36 may control a back-lighting unit 74, which, in turn, provides a light source that is transmitted through or around the Amsler grid 20 and/or the optotype chart 22, allowing the patient to easily view the Amsler grid 20 and/or optotype chart 22 in darkened conditions. Overall, a centrally-controlled and internally communicating circuit is contained in the housing 12.

The simultaneous flash and timer switch 14 and the timer stop switch 16 both interact, via the logic controller 36, with the internal components of the device 10. The simultaneous flash and timer switch 14, when actuated, discharges dazzling light, via the flash lamp 44, and begins a timing mechanism 76, which is either part of or external to the logic controller 36. A second control, the timer stop switch 16 both stops the timing mechanism 76, allowing the operator to read the timer visual display 24, and resets the timing mechanism 76 and timer visual display 24 with a second actuation. The on/off switch 30 allows the operator to sequence through the operations of device 10 to completion of the test on the patient. While the on/off switch 30 of the present invention 10 is a single-position-single throw, momentary closed push-button, used in controlling the device 10, any suitable switch or control is envisioned. It is also envisioned that one switch may be utilized to control some or all of the on/off function, the flash function, the timer begin function, the timer stop function, and the timer reset function. In a second embodiment, the simultaneous flash and timer switch 14 and the timer stop switch 16 are controlled through one multi-purpose switch 84 or button, as shown in FIG. 3. In this embodiment, all three functions are controlled by the multi-purpose switch 84, which communicates directly with the logic controller 36.

The logic controller 36 controls the sequencing of the operation of device 10, and, further, controls or is integral with the timing mechanism 76 that measures the patient response. The logic controller 36 can be the decoded logic source or provide logic output to a dedicated controller that will control the timer visual display 24. The timer visual display 24 may be a liquid crystal display or any suitable display type. Additionally, the logic controller 36 controls the charging, firing and safety discharge of the flash lamp 44, and can also be used to monitor the electronic health of the device 10 and control and monitor the power to the device 10. If, after a predetermined time, the logic controller 36 senses no function initiated by the operator, the logic controller 36 can discharge the flash lamp 44, if needed, depending on the type of flash lamp 44 utilized, and turn the overall device 10 power off.

Device 10 may use a linear xenon flash tube, or any suitable substitute, together with a suitable reflector to generate a spectrally distributed flash of light of an intensity sufficient to stress the macula of the patient, projecting out to the patient through a flash unit screen 18. Other light sources are envisioned, including an incandescent light or a light emitting diode. The light source can be comprised of a device that utilizes the photons that result from the transition of electrons from a higher energy state to a lower energy state as a result of exciting a suitable molecular or atomic structure. In using the linear xenon flash tube, the logic controller 36 sends a charge signal 24 to the flash controller unit 46, which has a storage capacitor 82. The flash controller unit 46 also triggers the flash lamp 44 at the command of the operator. The logic controller 36 may also be used to monitor the state of charge of the storage capacitor 82 and provide an indication to the operator when there is sufficient energy available to trigger the flash lamp 44. Further, the logic controller 36 may be used to prevent triggering of the flash lamp 44 until a required energy level is reached. The logic controller 36 could also communicate with a circuit which would allow the logic controller 36 to discharge the storage capacitor 82 if the time after the last operator-controlled function exceeded a predetermined time.

The logic controller 36 can disable power to the device 10 if there is no operator-initiated control after a predetermined time (i.e., five minutes of non-use). Also, the logic controller 36 can be used to indicate to the operator that the power source 32 is not sufficiently energized for operation of the device 10, or that the power source 32 is near a point of energy depletion. The power source 32 may be batteries, direct connection to external power, rechargeable batteries, or other well-known power sources.

Turning to the method of using the present invention 10, the device 10 is turned on via the on/off switch 30. Once activated, and if so desired, the backlighting unit 74 illuminates the Amsler grid 20 and the optotype chart 22 from within the device 10. When the flash controller unit 46, communicating with the logic controller 36, displays, communicates or otherwise indicates to the operator that the device 10 is ready for use, the operator engages the patient.

One of the patient's eyes is occluded, and the patient is asked to read the smallest line that the patient finds definable on the optotype chart 22. This step is completed while the patient continues wearing his or her adequate reading correction, if required. In addition, the optotype chart 22 is read at a typical reading distance, i.e., approximately 13–16 inches. The operator may use the retractable tape or string mechanism 26 to measure the distance from the device 10 to the patient; pulling out the tape to measure from the tip of the device 10 to the middle of the patient's eyes. The line that the patient is able to read is recorded in near point Snellen or any other standard ophthalmic terms.

Next, the patient removes his or her optical reading correction, if required. The device 10 is moved to approximately six inches, or another standardized distance, from the non-occluded eye, again using the retractable tape or string mechanism 26. The operator then instructs the patient to gaze to the center of the flash unit screen 18, and the operator then actuates the simultaneous flash and timer switch 14, discharging the flash lamp 44 and starting the timing mechanism 76, as indicated on the timer visual display 24. The patient is then instructed to replace any optical reading correction.

The device 10 is then placed back at its original "reading" distance, as measured by using the retractable tape or string mechanism 26. The patient's dazzled eye begins recovery, and the patient is directed to attempt to read the line immediately above the initially-read line of optotypes on the optotype chart 22. For example, if the patient read the 20/25 line on the optotype chart 22, the subject is now directed to focus on and attempt to read the 20/30 line on the optotype chart 22. When the patient is able to read the line, the operator actuates the timer stop switch 16, which stops the timing mechanism 76 and displays the recorded time on the timer visual display 24. The timer stop switch 16 is depressed again, resetting the timing mechanism 76 and clearing the timer visual display 24. The process is then repeated with the other formerly occluded eye.

Overall, the present invention 10 provides a portable, hand-held photostress testing apparatus that is elementary in operation and inexpensive in construction. Further, the present invention 10 is of the size and cost so as to allow for mass distribution to doctors, operators, acadamiens, and other parties in both clinical and research settings. Through such standardization and distribution of the present invention 10, it is anticipated that great strides in retinal disease studies may be made through the collection and study of the data received from the widespread use of the device 10. In addition, the portability and ease of use of the present invention 10, coupled with its inexpensive manufacture and standalone capabilities, will assist in advancing the art in the areas of macular degeneration and other diagnosable retinal disorders. Use of this device 10 will allow the doctor to detect and forewarn patients with a tendency to maculopathy.

The invention itself, both as to its construction and its method of operation, together with the additional objects and advantages thereof, will best be understood from the previous description of specific embodiments when read in connection with the accompanying drawings. It will be evident to those of ordinary skill in the art that various changes and modifications may be made to the present invention without departing from the spirit and scope thereof. For example, the portable housing may be formed with a table supported base and flip-top display similar to a laptop computer design. The specific embodiment described is intended to be illustrative of, and not restrictive of, the present invention. The present invention is defined by the appended claims and equivalents thereto.

I claim:

1. A visual examination apparatus for bleaching the human retina and measuring the recovery time of the retina, comprising:
   a portable housing adapted to be manually positioned in an operating position by the operator;
   a flash mechanism positioned within the portable housing, the flash mechanism adapted to emit a flash of light from the apparatus;
   a timing mechanism positioned within the portable housing, the timing mechanism adapted to calculate and record elapsed time; and
   an input device positioned within the portable housing having at least one input, the input device, when actuated, communicates with the flash mechanism and the timing mechanism, wherein a first input simultaneously triggers the flash mechanism and starts the timing mechanism, and a second input stops the timing mechanism.

2. The apparatus of claim 1, wherein at least one optotype chart is positioned on the portable housing, the at least one optotype chart adapted to fit on a face of the portable housing.

3. The apparatus of claim 2, further comprising a back-lighting mechanism positioned within the portable housing, the back-lighting mechanism adapted to illuminate through and around the at least one optotype chart.

4. The apparatus of claim 1, further comprising a measurement device integral with the portable housing, the measurement device adapted to allow a user to accurately measure the distance between the apparatus and a patient.

5. The apparatus of claim 1, further comprising a timer visual display positioned on a face of the portable housing, the timer visual display adapted to communicate with the timing mechanism and display elapsed time.

6. The apparatus of claim 1, further comprising a logic controller positioned within the portable housing, the logic controller adapted to communicate with and control the flash mechanism, the timing mechanism and the input device.

7. The apparatus of claim 6, wherein the logic controller will turn the apparatus off after sensing no operator input or no apparatus operation for a predetermined period of time.

8. The apparatus of claim 6, wherein the logic controller monitors and indicates to the operator the status of apparatus power.

9. The apparatus of claim 1, wherein a third input resets the timing mechanism.

10. A visual examination apparatus for bleaching the human retina and measuring the recovery time of the retina, comprising:

a hand-held housing adapted to be easily held by a user during operation of the apparatus;

a flash mechanism positioned within the hand-held housing, the flash mechanism adapted to emit a flash of light from the apparatus;

a timing mechanism positioned within the hand-held housing, the timing mechanism adapted to calculate and record elapsed time; and an input device positioned within the hand-held housing having at least one input, the input device, when actuated, communicates with the flash mechanism and the timing mechanism, wherein a first input simultaneously triggers the flash mechanism and starts the timing mechanism, and a second input stops the timing mechanism.

11. The apparatus of claim 10, wherein at least one optotype chart is positioned on the hand-held housing, the at least one optotype chart adapted to fit on a face of the hand-held housing.

12. The apparatus of claim 11, further comprising a back-lighting mechanism positioned within the hand-held housing, the back-lighting mechanism adapted to illuminate through and around the at least one optotype chart.

13. The apparatus of claim 10, further comprising a retractable measurement device integral with the hand-held housing, the retractable measurement device adapted to allow a user to accurately measure the distance between the apparatus and a patient.

14. The apparatus of claim 10, further comprising a timer visual display positioned on a face of the hand-held housing, the timer visual display adapted to communicate with the timing mechanism and display elapsed time.

15. The apparatus of claim 10, further comprising a logic controller positioned within the hand-held housing, the logic controller adapted to communicate with and control the flash mechanism, the timing mechanism and the input device.

16. The apparatus of claim 15, wherein the logic controller will turn the apparatus off after sensing no operator input or no apparatus operation for a predetermined period of time.

17. The apparatus of claim 15, wherein the logic controller monitors and indicates to the operator the status of apparatus power.

18. The apparatus of claim 10, wherein a third input resets the timing mechanism.

19. A method of testing the recovery time for a retina, comprising the steps of:

providing an apparatus including a portable housing, a flash mechanism positioned within the portable housing, a timing mechanism positioned within the portable housing, and an optotype chart having at least one line of optotypes thereon;

occluding one eye of a patient;

positioning the apparatus at a typical reading distance from a patient;

reading, by the patient, of a line of optotypes on the optotype chart;

positioning the apparatus to a closer position in front of the non-occluded eye of the patient;

actuating the apparatus to simultaneously trigger the flash mechanism and start the timing mechanism;

positioning the apparatus at a typical reading distance from the patient;

reading, by the patient, of a second line of optotypes on the optotype chart;

actuating the apparatus to stop the timing mechanism; and recording the recovery time.

20. The method of claim 19, further comprising the steps of:

removing any optical reading correction prior to actuating the first input; and replacing the reading correction prior to attempting to read the second line of optotypes on the optotype chart.

* * * * *